United States Patent
Couse et al.

(10) Patent No.: US 9,618,458 B2
(45) Date of Patent: Apr. 11, 2017

(54) OPTICAL MEASUREMENT METHOD AND APPARATUS FOR FUEL CELL COMPONENTS

(71) Applicant: Bloom Energy Corporation, Sunnyvale, CA (US)

(72) Inventors: Stephen Couse, Sunnyvale, CA (US); Tulin Akin, Sunnyvale, CA (US)

(73) Assignee: BLOOM ENERGY CORPORATION, Sunnyvale, CA (US)

(*) Notice: Subject to any disclaimer, the term of this patent is extended or adjusted under 35 U.S.C. 154(b) by 214 days.

(21) Appl. No.: 14/147,785

(22) Filed: Jan. 6, 2014

(65) Prior Publication Data

US 2014/0193064 A1    Jul. 10, 2014

Related U.S. Application Data

(60) Provisional application No. 61/750,136, filed on Jan. 8, 2013.

(51) Int. Cl.
| | |
|---|---|
| *G06K 9/00* | (2006.01) |
| *G01N 21/88* | (2006.01) |
| *G01B 11/24* | (2006.01) |
| *G06T 7/00* | (2017.01) |

(52) U.S. Cl.
CPC ......... *G01N 21/8851* (2013.01); *G01B 11/24* (2013.01); *G06T 7/0006* (2013.01); *G06T 2207/10028* (2013.01)

(58) Field of Classification Search
None
See application file for complete search history.

(56) References Cited

U.S. PATENT DOCUMENTS

| | | | |
|---|---|---|---|
| 2,176,784 A | 10/1939 | Bowden | |
| 5,550,763 A * | 8/1996 | Michael | ................ G01N 21/88 348/87 |
| 5,589,772 A | 12/1996 | Kugai | |
| 6,426,161 B1 | 7/2002 | Cisar et al. | |
| 6,599,651 B1 | 7/2003 | Saitou et al. | |

(Continued)

FOREIGN PATENT DOCUMENTS

| | | |
|---|---|---|
| JP | 2000-285934 A | 10/2000 |
| JP | 2007-042406 A | 2/2007 |
| KR | 10-2010-0109253 A | 10/2010 |

OTHER PUBLICATIONS

Muralikrishnan, Bala, et al. "Dimensional metrology of bipolar fuel cell plates using laser spot triangulation probes." Measurement Science and Technology 22.7 (2011): 075102.*

(Continued)

*Primary Examiner* — Sean Conner
(74) *Attorney, Agent, or Firm* — The Marbury Law Group PLLC

(57) ABSTRACT

Methods and systems for measuring a property of a component of a fuel cell system include performing a three-dimensional optical scan of at least a portion of a surface of the component to produce a three-dimensional representation of the topography of the at least a portion of the surface and measuring at least one property of the component based on the three-dimensional representation. Further embodiments include systems and methods for measuring dimensions of a fuel cell component using a line scan imaging device and/or a matrix camera.

14 Claims, 12 Drawing Sheets

(56) References Cited

U.S. PATENT DOCUMENTS

| | | | |
|---|---|---|---|
| 2004/0095127 A1 | 5/2004 | Mohri et al. | |
| 2004/0153979 A1* | 8/2004 | Chang | G06F 17/5068 716/56 |
| 2005/0069191 A1* | 3/2005 | Van Der Meer | G01N 21/9036 382/142 |
| 2005/0142431 A1 | 6/2005 | Shimomura et al. | |
| 2006/0127711 A1 | 6/2006 | Kaschmitter et al. | |
| 2006/0228613 A1 | 10/2006 | Bourgeois et al. | |
| 2008/0165924 A1* | 7/2008 | Wang | G01N 23/04 378/27 |
| 2008/0199738 A1 | 8/2008 | Perry et al. | |
| 2009/0214909 A1* | 8/2009 | Igarashi | H01M 8/04097 429/421 |
| 2010/0221837 A1* | 9/2010 | Uchiyama | B01D 65/102 436/3 |
| 2012/0086800 A1* | 4/2012 | Vladimirsky | B82Y 10/00 348/128 |
| 2012/0135337 A1 | 5/2012 | Herchen et al. | |
| 2012/0170052 A1* | 7/2012 | Kuo | G01B 11/0691 356/602 |

OTHER PUBLICATIONS

Sun, Chunwen, Rob Hui, and Justin Roller. "Cathode materials for solid oxide fuel cells: a review." J Solid State Electrochem 14.7 (2009): 1125-1144.*

International Search Report & Written Opinion, International Application No. PCT/US2011/062328, Aug. 1, 2012.

Huth et al., "Lock-in IR-Thermography—a novel tool for material and device characterization," Solid State Phenomena 82-84, pp. 741-746 (2002).

U.S. Appl. No. 14/149,187, filed Jan. 7, 2014, "Serialization of Fuel Cell Components," Stephen Couse et al., Specification and drawings.

Low Cost, High Efficiency Reversible Fuel Cell (and Electrolyzer) Systems, Proceedings of the 2001 DOE Hydrogen Program Review NREL/CP-570-30535.

Fialkov et al., "Diamagnetic Susceptibility and Linear Thermal Expansion of Graphitized Carbons," Soviet Powder Metallurgy and Metal Ceramics, vol. 4, No. 8, pp. 674-680.

International Search Report, International Application No. PCT/2013/035895, Jul. 25, 2013.

* cited by examiner

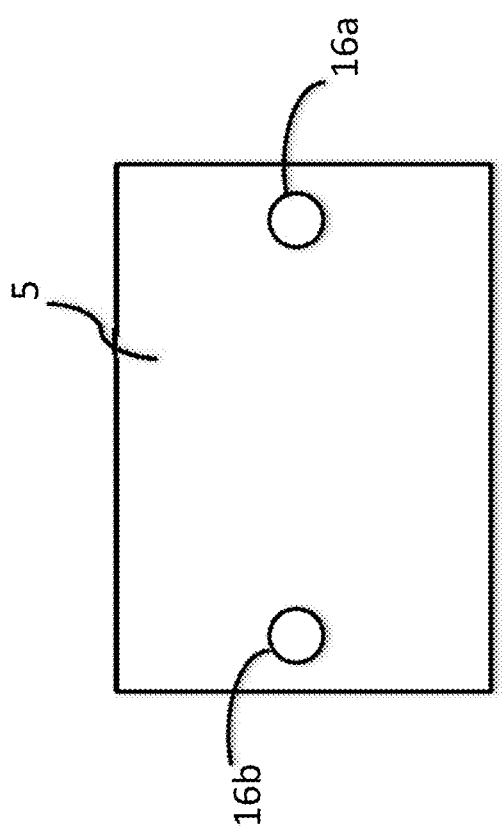
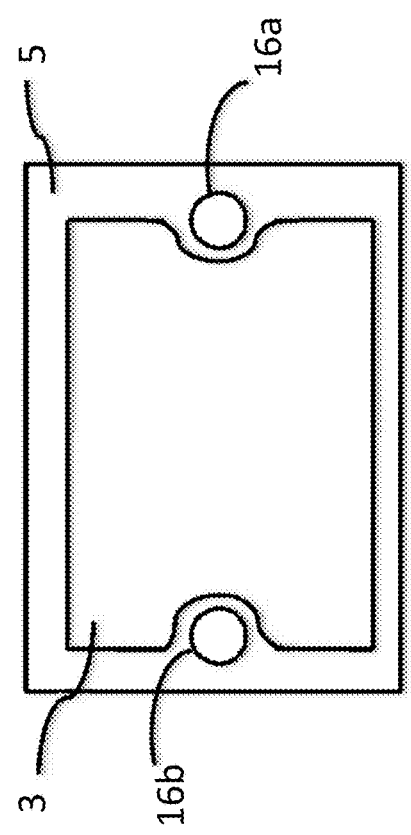
FIG. 2A
FIG. 2B

OPTICAL MEASUREMENT METHOD AND APPARATUS FOR FUEL CELL COMPONENTS

CROSS REFERENCE TO RELATED APPLICATION

This application claims the benefit of priority to U.S. Provisional Patent Application Ser. No. 61/750,136 entitled "Optical Measurement Method and Apparatus for Fuel Cell Components" filed Jan. 8, 2013, which is incorporated herein by reference in its entirety.

BACKGROUND

In a high temperature fuel cell system, such as a solid oxide fuel cell (SOFC) system, an oxidizing flow is passed through the cathode side of the fuel cell while a fuel flow is passed through the anode side of the fuel cell. The oxidizing flow is typically air, while the fuel flow can be a hydrocarbon fuel, such as methane, natural gas, pentane, ethanol, or methanol. The fuel cell, operating at a typical temperature between 750° C. and 950° C., enables the transport of negatively charged oxygen ions from the cathode flow stream to the anode flow stream, where the ion combines with either free hydrogen or hydrogen in a hydrocarbon molecule to form water vapor and/or with carbon monoxide to form carbon dioxide. The excess electrons from the negatively charged ion are routed back to the cathode side of the fuel cell through an electrical circuit completed between anode and cathode, resulting in an electrical current flow through the circuit.

In order to optimize the operation of SOFCs, the various components of the system, such as the electrolyte, the anode and cathode electrodes and interconnects should be precisely manufactured and generally free of defects.

SUMMARY

Various embodiments include methods for measuring a property of a component of a fuel cell system that include performing a three-dimensional optical scan of at least a portion of a surface of the component to produce a three-dimensional representation of the topography of the at least a portion of the surface; and measuring at least one property of the component based on the three-dimensional representation.

Further embodiments include methods of measuring a dimension of a component of a fuel cell system that include obtaining at least one image of the component using at least one of a line scan imaging device and a matrix camera, and measuring a dimension of the component based on the at least one obtained image.

Further embodiments include systems for performing the above-described measurements of a component of a fuel cell system.

BRIEF DESCRIPTION OF THE DRAWINGS

The accompanying drawings, which are incorporated herein and constitute part of this specification, illustrate example embodiments of the invention, and together with the general description given above and the detailed description given below, serve to explain the features of the invention.

FIG. 2A is a plan view of an electrolyte of a fuel cell.

FIG. 2B is a plan view of an electrolyte and an electrode of a fuel cell.

DETAILED DESCRIPTION

Figure 1A:
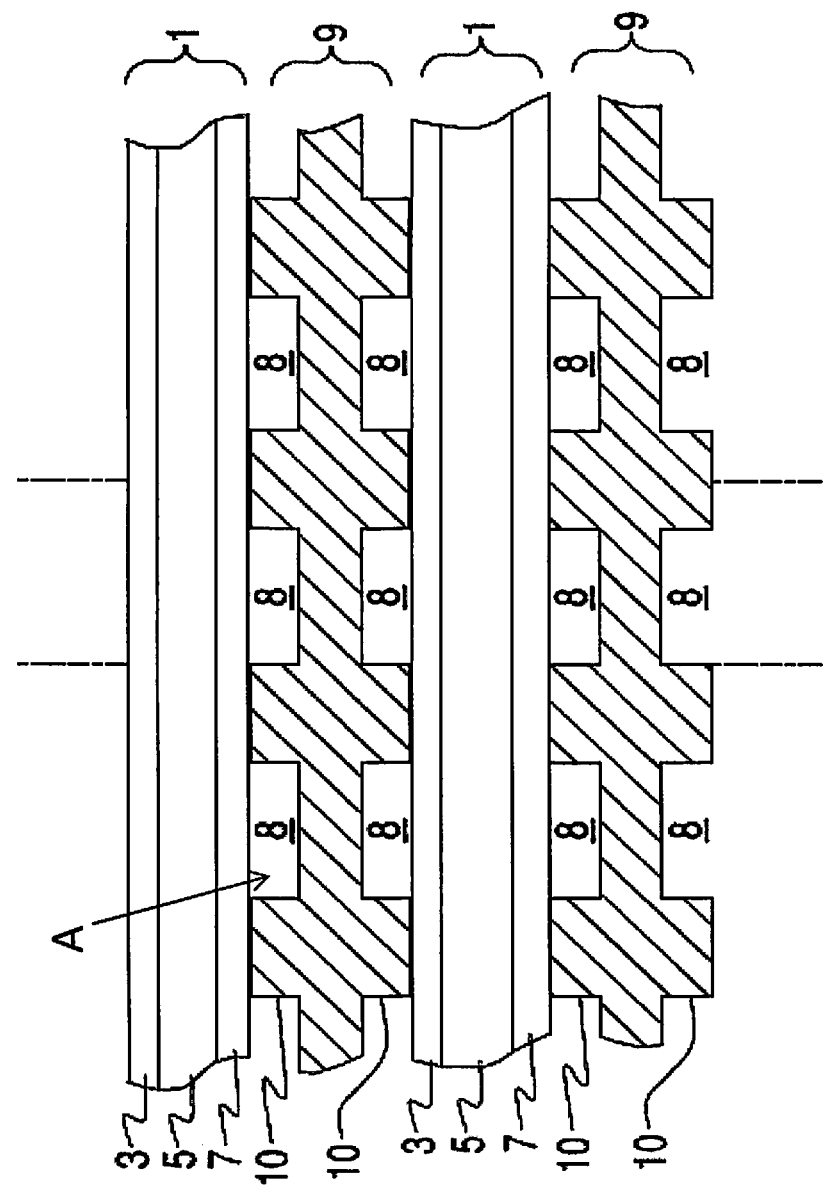
FIG. 1A illustrates a side cross-sectional view of a SOFC stack.

The various embodiments will be described in detail with reference to the accompanying drawings. Wherever possible, the same reference numbers will be used throughout the drawings to refer to the same or like parts. References made to particular examples and implementations are for illustrative purposes, and are not intended to limit the scope of the invention or the claims.

In one aspect, the present invention provides accurate, rapid and non-destructive techniques for measuring properties of components of fuel cell systems, including fuel cells and interconnects, which are expected to greatly improve the fabrication process for solid oxide fuel cell systems. It is anticipated that the present detection technique will result in lower costs for these systems, since various properties of the components of the system may be more effectively characterized and defective components and cells can be more easily identified and removed at an earlier stage of production and/or use. Furthermore, the present fuel cell system component measurement methodology should help lower production costs of many fuel cell systems, since the current labor-intensive and time-consuming inspection processes can now be avoided.

FIG. 1 illustrates a SOFC stack in which each SOFC 1 comprises a cathode electrode 7, a solid oxide electrolyte 5, and an anode electrode 3. Fuel cell stacks are frequently built from a multiplicity of SOFC's 1 in the form of planar elements, tubes, or other geometries. Fuel and air has to be provided to the electrochemically active surface, which can be large.

The gas flow separator 9 (referred to as a gas flow separator plate when part of a planar stack), containing gas flow passages or channels 8 between ribs 10, separates the individual cells in the stack. The gas flow separator plate separates fuel, such as a hydrocarbon fuel, flowing to the fuel electrode (i.e. anode 3) of one cell in the stack from oxidant, such as air, flowing to the air electrode (i.e. cathode 7) of an adjacent cell in the stack. At either end of the stack, there may be an air end plate or fuel end plate (not shown) for providing air or fuel, respectively, to the end electrode.

Frequently, the gas flow separator plate 9 is also used as an interconnect which electrically connects the anode or fuel electrode 3 of one cell to the cathode or air electrode 7 of the adjacent cell. In this case, the gas flow separator plate which functions as an interconnect is made of or contains electrically conductive material. FIG. 1 shows that the lower SOFC 1 is located between two interconnects 9.

Figure 1B:
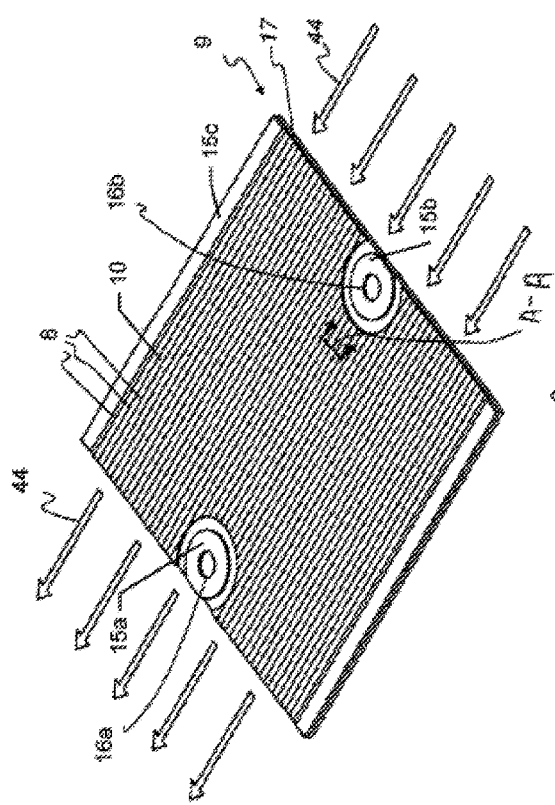
FIGS. 1B and 1C show, respectively, top and bottom views of an interconnect for a SOFC stack.
Figure 1C:
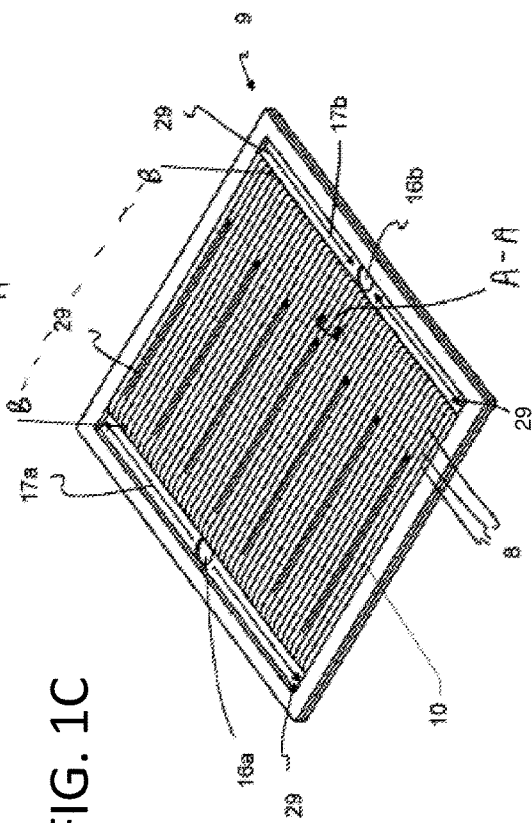

FIGS. 1B and 1C show, respectively, top and bottom views of an interconnect 9. The portions of interconnect 9 shown in side cross-section in FIG. 1A are provided along lines A-A in FIGS. 1B and 1C. The interconnect 9 contains gas flow passages or channels 8 between ribs 10. The interconnect 9 in this embodiment includes at least one riser channel 16a for providing fuel to the anode-side of the SOFC 1, as illustrated by arrow 29. The riser channel 16a generally comprises a fuel inlet riser opening or hole that extends through at least one layer of the fuel cells and interconnects in the stack. As illustrated in FIG. 1C, the fuel can flow through the inlet riser channel 16a to the anode-side of each fuel cell. There, the fuel can collect in an inlet plenum 17a (e.g., a groove in the interconnect's surface), then flow over the fuel cell anode 3 through gas flow channels 8 formed in the interconnect 9 to an outlet plenum 17b and then exit through a separate outlet riser channel 16b.

The cathode side, illustrated in FIG. 1B, can include gas flow passages or channels 8 between ribs 10 which direct air flow 44 over the cathode electrode of the fuel cell. Seals 15a, 15b can seal the respective risers 16a, 16b on the cathode-sides of the interconnect and fuel cell to prevent fuel from reaching the cathode electrode of the fuel cell. The seals may have a donut or hollow cylinder shape as shown so that the risers 16a, 16b extend through the hollow middle part of the respective seals 15a, 15b. The seals 15a, 15b can include a elevated top surface for contacting against the flat surface of the adjacent SOFC 1. A peripheral seal 15c can seal the anode-sides of the interconnect and fuel cell to prevent air from reaching the anode electrode of the fuel cell.

An interconnect 9 may be a chromium-based alloy such as 4-6 wt % Fe and 94-96 wt % Cr, with optionally less than about 1 wt % of Y and unavoidable impurities, and may be formed using a powder metallurgy technique. A protective coating (e.g., a lanthanum strontium manganite (LSM) perovskite coating and/or manganese cobalt oxide (MCO) spinel coating) may be formed over at least one surface of the interconnect 9, such as over the cathode-facing surface of the interconnect 9.

FIG. 2A is a plan view of a solid oxide electrolyte 5. The electrolyte 5 may comprise a stabilized zirconia, such as scandia stabilized zirconia (SSZ) or yttria stabilized zirconia (YSZ). Alternatively, the electrolyte 5 may comprise another ionically conductive material, such as a doped ceria. In this embodiment, the electrolyte 5 has a planar geometry, although it will be understood that other geometries, such as a tubular geometry, could be utilized. Riser channel openings 16a, 16b, which in this embodiment comprise circular holes, extend through the electrolyte 5. The riser channels 16a, 16b generally comprise fuel inlet and outlet openings that extend through at least one layer of the fuel cells. The riser channels 16a, 16b can extend through multiple electrolyte layers 5 and interconnects 9 between the electrolyte layers in a fuel cell stack. Fuel can flow through the inlet riser channel 16a to the anode-side of each fuel cell. There, the fuel flows over the fuel cell anode 3 via gas flow channels 8 formed in the gas flow separator/interconnect plate 9, and then exits through separate outlet riser channel 16b.

In FIG. 2B, an anode (e.g., fuel) electrode 3 is shown covering part of a first major surface of the electrolyte 5. A cathode (e.g., air) electrode 7 (not shown) can cover part of the second major surface on the opposite side of the electrolyte 5.

The SOFC 1 in this embodiment is configured for a stack that is internally manifolded for fuel and externally manifolded for air. Thus, the stack is open on the air inlet and outlet sides. Alternatively, the SOFC 1 may be configured for a stack which is internally manifolded for both air and fuel. In this case, the electrolyte would contain additional air inlet and outlet openings. Alternatively, the SOFC 1 may be externally manifolded for air and fuel.

The various fuel cell components must be precisely manufactured to maximize fuel cell efficiency. The fuel cell components should also be substantially free of defects, including small cracks in the components, coating defects and non-uniform topography. The various components in a fuel cell stack, such as the interconnects, should also have relative dimensional uniformity.

Figure 3A:
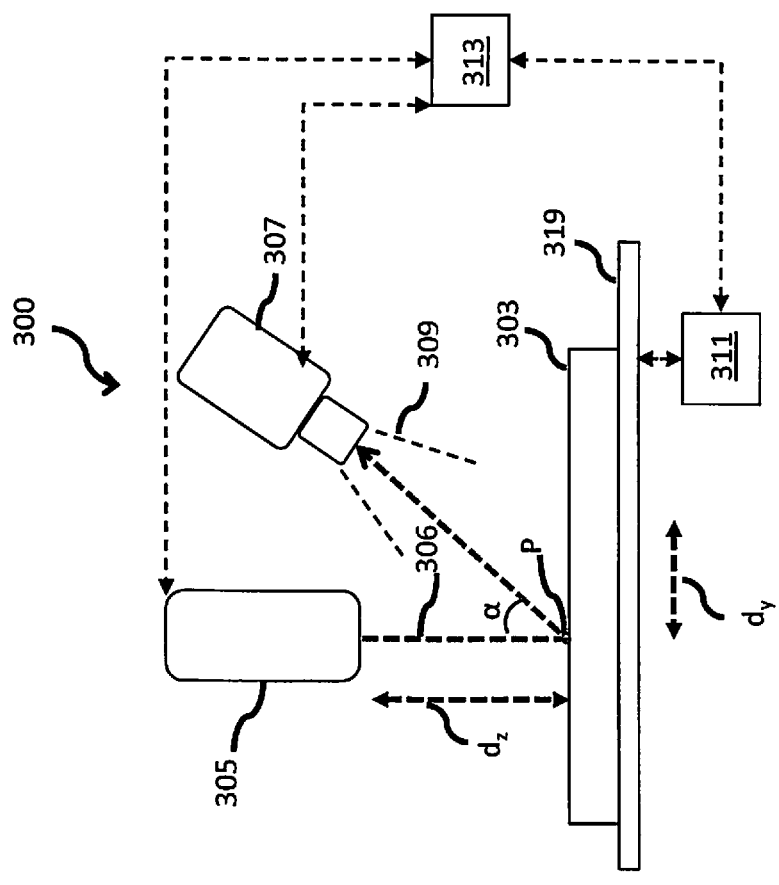
FIG. 3A is a side view of a fuel cell component and laser triangulation measurement apparatus according to one embodiment.
Figure 3B:
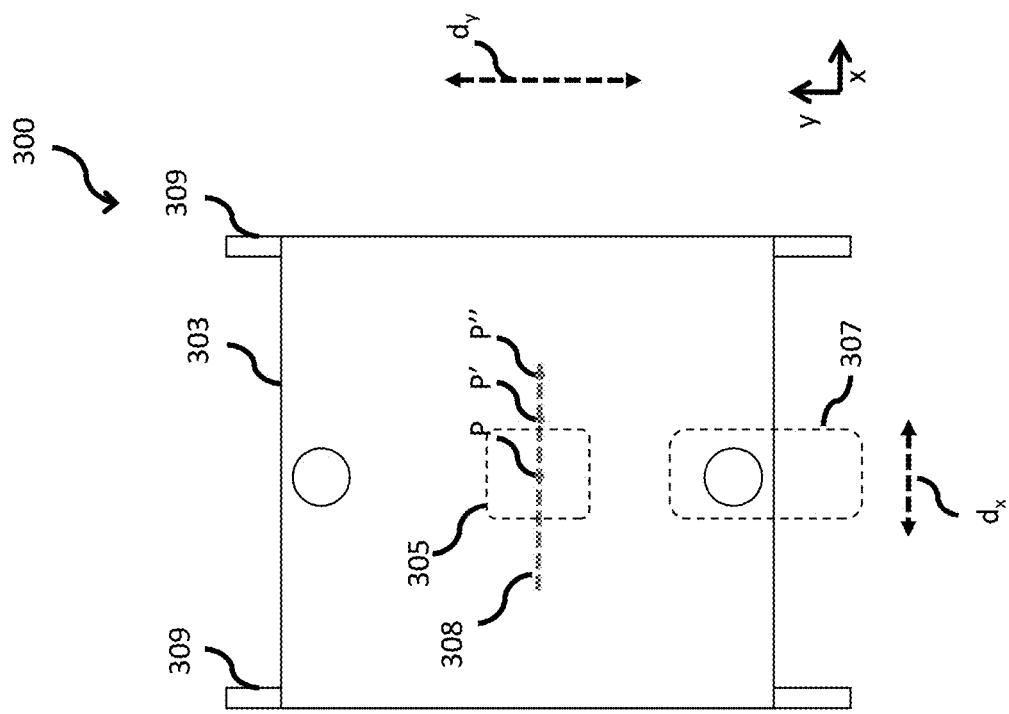
FIG. 3B is an overhead view of the fuel cell component and laser triangulation measurement apparatus of FIG. 3A.

FIGS. 3A and 3B schematically illustrate a system 300 for measuring a property of a component of a fuel cell system using optical triangulation. In one embodiment, as shown in the side-view of FIG. 3A, the system 300 includes a source 305 for directing an optical radiation beam 306 onto a fuel cell component 303. An optical detector 307, such as a camera, is positioned to detect radiation reflected from the surface of the fuel cell component 303. The source may be a laser source that generates a laser beam, which may be single beam that projects a single point (i.e., laser dot) on the surface of the component 303, or may simultaneously project a plurality of contiguous or non-contiguous points, such as a line 308 as shown in the overhead view of FIG. 3B. (The source 305 and detector 307 are shown in phantom in FIG. 3B to more clearly illustrate the line 308 and fuel cell component 303). In some embodiments, the component 303 of a fuel cell system can be an interconnect for a fuel cell stack, such as interconnect 9 shown in FIGS. 1A-1C. The component 303 can also be an electrolyte plate or layer, including raw electrolyte material, or an electrolyte plate or layer having one or more electrodes provided on the electrolyte, and can be a finished cell, such as SOFC 1 shown in FIGS. 1 and 2B.

The system 300 may use optical triangulation (e.g., laser triangulation) to measure one or more properties of the component 303. In an optical triangulation technique, an optical radiation source 305 (e.g., a laser source) directs a beam 306 onto a component 303, and a detector 307 (e.g., a camera) detects radiation (e.g., a laser dot) reflected from at least one point (P) on the surface of the component 303. Depending on how far the beam travels from the source 306 before striking the surface of the component 303, the reflected radiation from a point P of the surface will appear at different places (e.g., different pixel locations) in the field of view 309 of the detector 307. The detector 307 typically includes a lens to focus the reflected beam onto the detector elements, which may comprise a CCD array, for example.

In an optical triangulation measurement, the source 305, the detector 307 and a point, P, on the surface of the component 303 being measured form a triangle. The source 305 and detector 307 may be in a fixed position and orientation relative to each other, and the distance between the source 305 and detector 307 (i.e., a first side of the triangle) and the angle at which the beam 306 is directed at the component 303 (i.e., one angle of the triangle) are known. A second angle of the triangle, the angle α at which the beam 306 is reflected from point P, may be determined based on the location of the laser dot in the field of view of the detector 307. These three pieces of information fully determine the shape and size of the triangle and gives the location of the corner of the triangle, corresponding to point P. The further away P is from the source 305 and detector 307, the smaller the angle α, and the closer point P is to the source 305 and detector 307, the larger the angle α.

As shown in FIG. 3A, a height or z-axis dimension of point P (i.e., the distance, $d_z$ between the point P and the source 305, corresponding to a second side of the triangle) may be measured using the triangulation technique. Alternatively, the distance between point P and the detector 307 (i.e., the third side of the triangle) can be measured. The interrogating beam 306 may be scanned across all or a portion of the surface of the component 303 while the detector 307 obtains z-axis measurements (i.e., $d_z$ measurements) of the surface to provide a three-dimensional representation of the topography of the component 303. For example, as shown in FIGS. 3A-B, the component 303 may be moved relative to the source 305 and detector 307 in a second direction (i.e., y-axis direction), orthogonal to the direction of the height measurements (i.e., z-axis measurements) to obtain $d_z$ measurements at different distances, $d_y$, along the y-axis dimension of the component 303. The interrogating beam 306 may produce a line 308 (see FIG. 3B) that scans across the surface of the component 303 in a third orthogonal direction (i.e., x-axis direction) to enable simultaneous $d_z$ measurements for an arbitrary number of points, P, P', P'' along the line 308. In embodiments, the line 308 may have sufficient length to scan the entire x-axis dimension of the component 303 in a single pass. In other embodiments, such as shown in FIG. 3B, the line 308 may be shorter than the x-axis dimension of the component 303, and the x-axis dimension of the component 303 may be scanned in multiple passes or by using multiple source 305 and detector 307 pairs arranged along the x-axis direction.

In embodiments, the beam 306 may be a focused optical beam (e.g., a laser beam) having a width of 20-100 µm in at least one direction (e.g., the y direction). The beam may be elongated in a second direction (e.g., the x-direction) and may have a length of 1-100 mm, for example, such as 30-50 mm (e.g., ~40 mm).

A support 319, such as a conveyer belt or a pair of rails, may support the component 303 during the measurement. A drive system 311 may be coupled to the support 319 for moving the component 303 during the measurement. As shown in FIGS. 3A-3B, the drive system 311 may move the component 303 along the y-axis direction. In other embodiments, the drive system 311 may additionally or alternatively move the component 303 along the x-axis direction. In addition, the drive system 311 may additionally or alternatively be coupled to the source 305 and detector 307 for moving the source 305 and detector 307 relative to the component 303.

In one embodiment, a controller 313 can be electronically coupled to the source 305 and detector 307, as shown in FIG. 3A. Controller 313 can be a logic device (e.g., computer) and can include a memory and a processor coupled to the memory, wherein the processor can be configured with processor-executable instructions for performing various functions. In one embodiment, the controller 313 is configured to control the operation of the source 305 and detector 307, and may be configured to cause the source 305 to direct an optical beam 306 to the component 303. The controller 313 may also be electronically coupled to the drive system 311 for controlling the movement of the component 303 relative to the source 305 and the detector 307 to perform a scan of the component 303 or of a portion thereof. The controller 313 may also be configured to receive image data from the detector 307, and based on the image data, to calculate the height (i.e., $d_z$) values for various points on the surface of the component 303 and to use these values to produce a three-dimensional representation of the topography of at least one surface of the component 303. The controller may also be configured to measure at least one property of the component 303 based on the three-dimensional topological representation, as described below.

Measuring Flow Channel Volume of Interconnects Using Optical Triangulation

A key to efficient operation of a fuel cell system is achieving high fuel utilization within a fuel cell stack and within a power generation system containing multiple stacks (i.e., a hotbox). Therefore good fuel distribution within a stack or within a column of stacks is critical. Manufacturing the interconnects for a fuel cell stack using a powder metallurgy technique is challenging and can result in a large dimensional variability in the interconnects, such as from batch to batch, vendor to vendor or over time through die wear. These dimensional variations can affect the flow properties of the interconnects, resulting in sub-optimal fuel distribution and reduced efficiency of a fuel cell stack or fuel cell system.

The flow properties of an interconnect or group of interconnects may be estimated by measuring the cross-sectional area (indicated "A" in FIG. 1A) of one or more flow channels 8 of the interconnect 9. The square of the area of the flow channels (i.e., $A^2$) has been found to be a useful proxy of the flow properties of the interconnect. However, current techniques for measuring flow channel cross-sectional area in interconnects are slow and do not measure the entire interconnect.

Various embodiments include a method for measuring a flow property of an interconnect for a fuel cell stack that includes performing a 3D optical scan of at least a portion of a surface of the interconnect containing at least one flow channel to produce a three-dimensional representation of the topography of the at least a portion of the surface, and calculating a volume of the at least one flow channel based on the three-dimensional representation. In embodiments, the 3D optical scan may be an optical triangulation scan, such as a laser triangulation scan, as shown in FIGS. 3A and 3B.

In embodiments, the 3D optical scan may be performed at plural locations over a surface of the interconnect, which may be an anode-facing surface of the interconnect, and a plurality of flow volumes from a single channel or from a plurality of channels may be calculated. In some embodiments, the entire flow field region of the interconnect may be scanned, and the volumes of all channels may be calculated along the entire length of the channels, or of portions thereof. In some embodiments, the volume of a channel may be approximated by measuring a series of cross-sectional areas of a channel and squaring them (i.e., $A^2$) to obtain a series of $A^2$ values for each channel. The optical scan may be performed of the anode-facing surface (i.e., fuel side) of the interconnect, the cathode-facing surface (i.e., air side), or both the anode- and cathode-facing surfaces of the interconnect, either sequentially using a single optical scanning system or simultaneously using multiple scanning systems disposed on either side of the interconnect. Other dimensional characteristics of the interconnect, such as, cross-sectional area and/or volume of a fuel plenum, radii of curvature, angles, heights and depths of various features, such as channels and ribs, may also be measured using three-dimensional optical scanning.

In this manner, the flow properties for an interconnect may be accurately and rapidly measured. A typical measurement to determine flow volume value(s) for all flow channels on a surface of an interconnect may take less than 10 seconds, such as 5 seconds or less (e.g., 1-4 seconds).

Detecting Cracks in Interconnects Using Optical Triangulation

Figure 4:
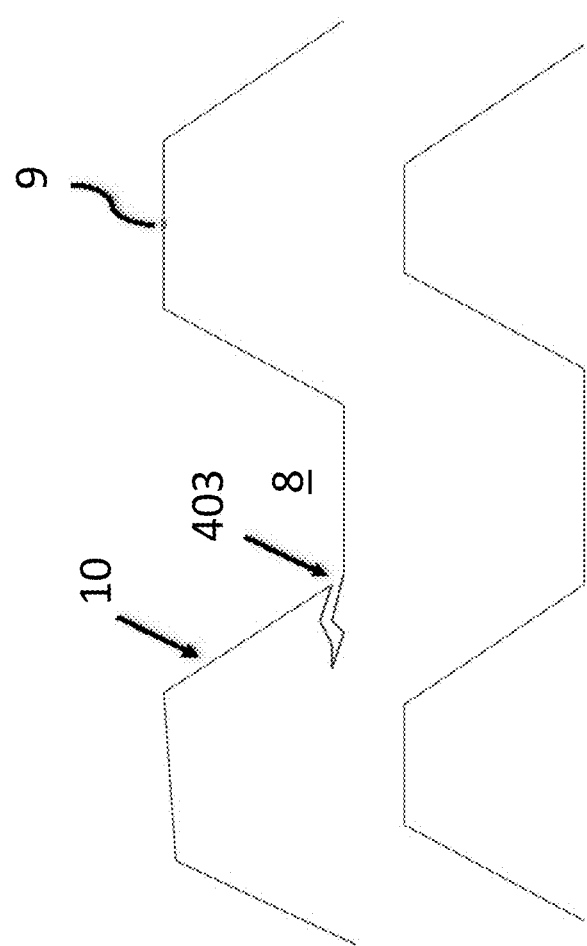
FIG. 4 schematically illustrates a laterally-extending crack defect in an interconnect for a fuel cell system.

In various embodiments, a 3D optical scan, such as an optical triangulation scan, may be used to detect defects in an interconnect for a fuel cell, including cracks in the interconnect. FIG. 4 schematically illustrates a cross-section of an interconnect 9. A crack 403 may form in the interconnect 9. One type of crack 403, shown in FIG. 4, extends generally parallel to the surface of the interconnect 9 (i.e., a lateral crack), and can extend from a flow channel 8 into a rib 10 of the interconnect 9, causing the rib 10 to become raised. This may produce a stress region on the fuel cell adjacent to the raised rib 10, significantly increasing the probability that the fragile fuel cell will crack. This kind of laterally-extending crack 403 may not be visible to the naked eye and is extremely difficult to detect using conventional testing techniques. Thus, it would be desirable to provide a rapid and accurate technique for detecting cracks in interconnects, such as lateral cracks, before the interconnects are incorporated into a fuel cell stack.

Various embodiments include a method for detecting defects in an interconnect for a fuel cell stack that includes performing a 3D optical scan of at least a portion of a surface of the interconnect containing at least one rib to produce a three-dimensional representation of the topography of the at least a portion of the surface, calculating a height of the rib based on the three-dimensional representation, and determining the presence or absence of a defect, such as a lateral crack, based on the calculated rib height. In embodiments, the 3D optical scan may be an optical triangulation scan, such as a laser triangulation scan, as shown in FIGS. 3A and 3B.

As shown in FIG. 4, a rib 10 with a crack 403 extending laterally through or beneath the rib stands higher than the neighboring ribs (e.g., by 30-50 micron for example). This difference in rib height may be detected using a 3D optical scanning technique, such as laser triangulation.

In embodiments, the 3D optical scan may be performed at plural locations over a surface of the interconnect, and a plurality of rib height values for a single rib or plurality of ribs may be measured. In some embodiments, the heights of all ribs may be measured. The optical scan may be performed of the anode-facing surface (i.e., fuel side) of the interconnect, the cathode-facing surface (i.e., air side), or both the anode- and cathode-facing surfaces of the interconnect, either sequentially using a single optical scanning system or simultaneously using multiple scanning systems disposed on either side of the interconnect. The measured rib height values may be compared to a reference rib height or range of measured rib heights, which may be based on an average of the measured rib heights for all ribs of an interconnect or from a plurality of interconnects. A defect may be detected when a measured rib height differs from a reference rib height by a predetermined amount or is outside of an expected range of rib heights. In some embodiments, each rib may be compared with its neighboring ribs, and a rib having a measured height that deviates from its neighbors by a predetermined amount may be flagged as defective.

In addition to measuring crack defects in an interconnect, the present method may also be used to detect ribs that are partially or completely missing, such as when the measured rib height is below an expected range of rib heights. The method may also be used to detect for other defects, such as holes or voids in an interconnect or other fuel cell components. In this manner, various defects in an interconnect may be accurately and rapidly measured. A typical measurement to detect defects in an interconnect may take less than 10 seconds, such as 5 seconds or less (e.g., 1-4 seconds).

Detecting Coating Defects Using Optical Triangulation

Figure 5:
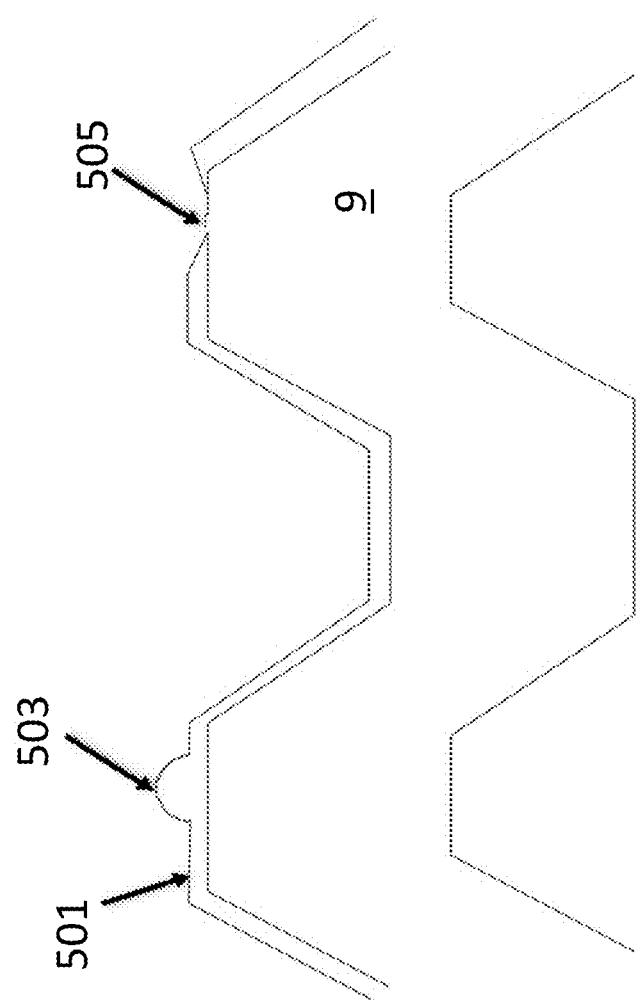
FIG. 5 schematically illustrates coating defects in an interconnect for a fuel cell system.

An interconnect for a fuel cell system, such as interconnect 9 shown in FIGS. 1A-C, may have a protective coating (e.g., a lanthanum strontium manganite (LSM) perovskite coating and/or a manganese cobalt oxide (MCO) spinel coating) formed over at least one surface of the interconnect 9, such as over the cathode-facing surface of the interconnect 9. The coating may be formed by a plasma spray coating process. FIG. 5 schematically illustrates an interconnect 9 having a protective coating 501 formed over a surface of the interconnect 9.

A coated interconnect 9 can have several types of coating defects. One type of defect is high points 503 (e.g., small bumps) of the coating 501 on the surface of the interconnect 9, which may be caused by the underlying interconnect material containing a high point that is coated by the protective coating or by the coating process itself resulting in high points due to splattering. These high points create a stress riser on fragile ceramic fuel cell adjacent to the high point. This stress riser significantly increases the probability of causing a crack in the fuel cell. These types of defects are very challenging to find using conventional vision systems of manual screening. Another type of coating defect is areas of missing or insufficient coating, such as coating void area 505 shown in FIG. 5.

Various embodiments include a method for detecting coating defects in an interconnect for a fuel cell stack that includes performing a 3D optical scan of at least a portion of a surface of the interconnect having a protective coating to produce a three-dimensional representation of the topography of the at least a portion of the surface, and determining the presence or absence of a coating defect, such as a coating high point or coating void area, based on the representation. Other coating defects, such as delamination of a coating on a fuel cell component, such as delamination of a protective coating on an interconnect and/or an electrode layer of a fuel cell electrolyte, may also be detected using a 3D optical scan. In embodiments, the 3D optical scan may be an optical triangulation scan, such as a laser triangulation scan, as shown in FIGS. 3A and 3B.

In embodiments, the 3D optical scan may be performed at plural locations over a coated surface of the interconnect, including over the entire interconnect. The optical scan may be performed of the cathode-facing surface (i.e., air side) of the interconnect, the anode-facing surface (i.e., fuel side), or both the cathode- and anode-facing surfaces of the interconnect, either sequentially using a single optical scanning system or simultaneously using multiple scanning systems disposed on either side of the interconnect. The measured height values of the coated interconnect may be compared to a reference height value or range of height values, which may be based on an average of height measurements from a coated interconnect or from a plurality of coated interconnects. The measured height values may be calibrated to help distinguish background topological features of the interconnect (e.g., ribs, channels, riser channel openings, etc.) from the contribution of the protective coating. For example, a surface of an interconnect may be optically scanned twice, including an initial scan of the interconnect prior to application of a protective coating, and a second scan after the protective coating is applied. The measured height values from the second scan may be calibrated by subtracting the corresponding measurements from the initial scan to provide an accurate measurement of the thickness of the protective coating.

A coating defect may be detected when a measured height value is above a threshold height value (indicating a coating high point defect) and/or below a threshold height value (indicating a coating void area defect). The threshold(s) may be further refined by measuring the areas of any detected coating high points and/or coating void areas. For example, a defect may be flagged when a detected high point or void area covers a region that is larger than a threshold surface area of the interconnect.

In this manner, various coating defects in an interconnect may be accurately and rapidly measured. A typical measurement to detect coating defects in an interconnect may take less than 10 seconds, such as 5 seconds or less (e.g., 1-4 seconds).

Measuring Thickness and Curvature of a Fuel Cell Component Using Optical Scanning One of the keys to an efficient fuel cell system is using conforming parts in the construction of the fuel cell stacks. The use of powder metallurgy techniques to fabricate the fuel cell interconnects is challenging and can result in significant dimensional variability in the interconnects, such as from batch to batch, vendor to vendor or over time through die wear. Similar dimensional variability may exist in the fuel cell electrolytes, which are typically made of fired ceramic material.

Thus, when constructing a fuel cell stack or multi-stack fuel cell power system, it is desirable to use components, such as interconnects and electrolytes, that share similar dimensional characteristics, such as thickness and curvature (camber). Current inspection techniques for measuring thickness and curvature of fuel cell components are very slow and do not measure the entire component.

Various embodiments include a method for measuring a dimensional property of a fuel cell component, such as thickness and/or curvature, using 3D optical scanning, such as optical triangulation (e.g., laser triangulation) scanning. The component may be an interconnect 9 for a fuel cell stack, such as shown in FIGS. 1A-C. The component may also be an electrolyte plate or layer, including raw electrolyte material, or an electrolyte plate or layer having one or more electrodes provided on the electrolyte, and can be a finished cell, such as SOFC 1 shown in FIGS. 1 and 2B.

Figure 6:
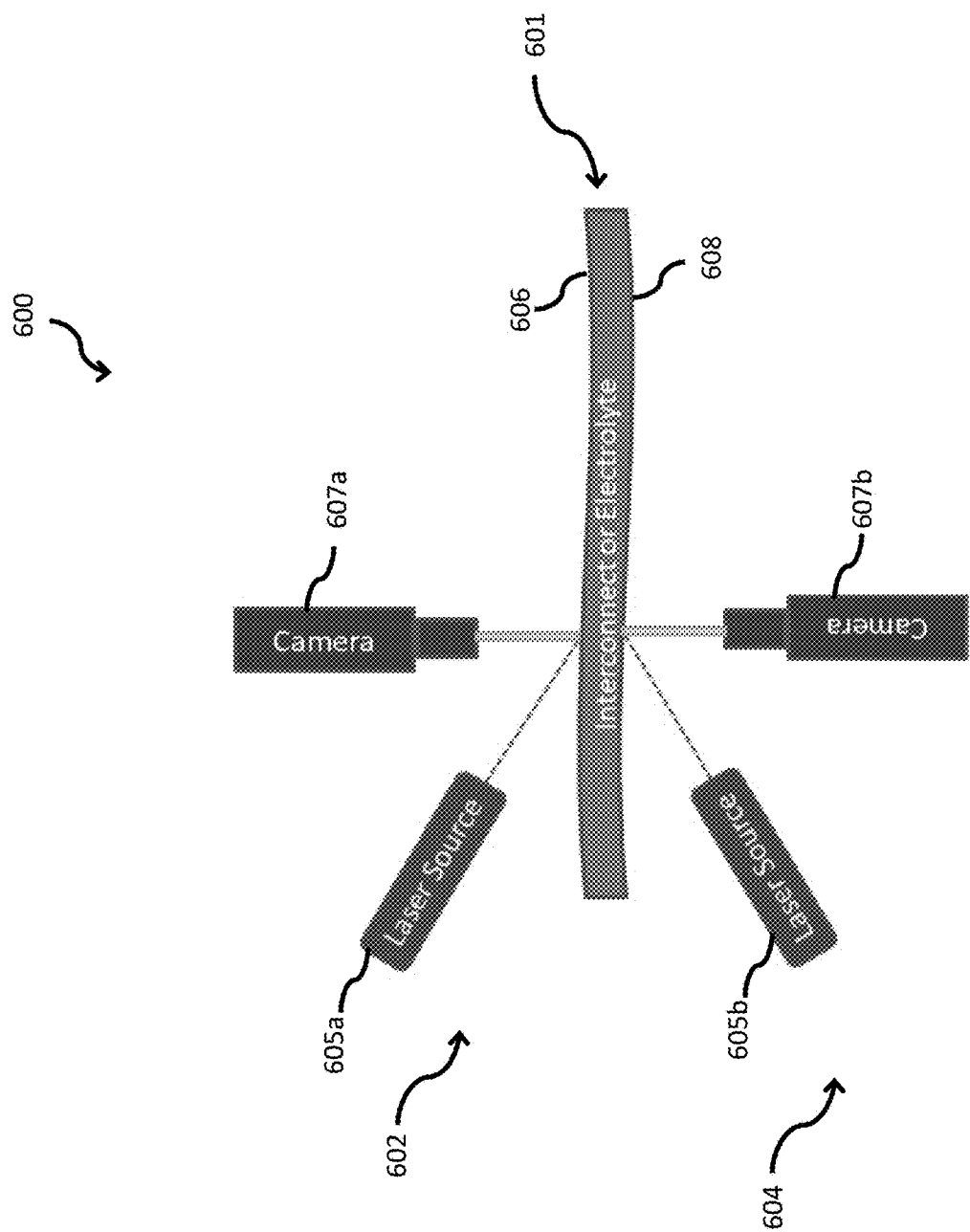
FIG. 6 schematically illustrates a system having an optical scanning device located on two opposing sides of a fuel cell component.

A system 600 for measuring a dimensional property of a fuel cell component 601, such as an interconnect or electrolyte (SOFC), is schematically illustrated in FIG. 6. The system 600 may include two optical scanning devices 602, 604 disposed on opposite sides of the component 601. Each scanning device 602, 604 may include a source 605a, 605b of optical radiation (e.g., a laser source) and a detector 607a, 607b, and may scan the respective surfaces 606, 608 of the component 601, using optical (laser) triangulation, for example, to produce a three-dimensional representation of the topography of the respective surfaces 606, 608 of the component 601, as described above in connection with FIGS. 3A-B. The measurements from both scanning devices 602, 604 may be combined and various algorithms may be used to calculate dimensional properties of the component 601, such as thickness and/or curvature of the component. In one embodiment, the various z-dimension measurements from the respective scanning devices 602, 604 may be translated into a common coordinate system. The thickness of the component 601 may then be determined by subtracting one set of measurements from the other. The overall curvature of the component 601 may also be determined using a suitable algorithm.

Thus, in embodiments, a method for measuring a dimensional property of the fuel cell component may include scanning a first surface of the component to produce a three-dimensional representation of the topography of the first surface, scanning a second surface of the component, opposite the first surface, to produce a three-dimensional representation of the topography of the second surface, and combining the three-dimensional representations of the topography of the first and second surfaces to measure a dimensional property of the component. In embodiments, the first scan and the second scan may occur simultaneously. The scans may be performed using a system 600 having scanning devices 602, 604 positioned on either side of the component 601, such as shown in FIG. 6. The component 601 may be supported on a support that permits simultaneous scanning of both sides of the component 601, such as the rail supports 309 shown in FIG. 3B, which may support the components 601 on their sides or edges.

In other embodiments, the first scan and the second scan may be performed sequentially. For example, a single optical scanning device could be used by scanning the first surface of the component, turning the component over, and running the component through the optical scanning device a second time to scan the second surface of the component.

In this manner, various dimensional properties of a fuel cell component, such as thickness and/or curvature, may be accurately and rapidly measured. A typical measurement to detect dimensional properties of a fuel cell component may take less than 10 seconds, such as 5 seconds or less (e.g., 1-4 seconds).

Measuring Topography of an Interconnect Using Optical Scanning

One of the important properties of an interconnect for a fuel cell system is the topography of the interconnect. Ideally, the topography should be relatively uniform throughout the interconnect. If the interconnect has local high and local low spots, it has been found that this has an effect on the stack yield due to increased stress on the adjacent fuel cell(s).

Interconnects are typically fabricated using a powder pressing metallurgy method. An interconnect can be a complex and challenging part to fabricate by this technique and can result in a large variability in topography from batch to batch, vendor to vendor or over time from die wear. Current techniques for measuring the topography of a powder pressed interconnect are deficient, in that they must be performed manually, take a relatively long time to perform, and do not measure the whole interconnect area adequately.

Figure 7A:
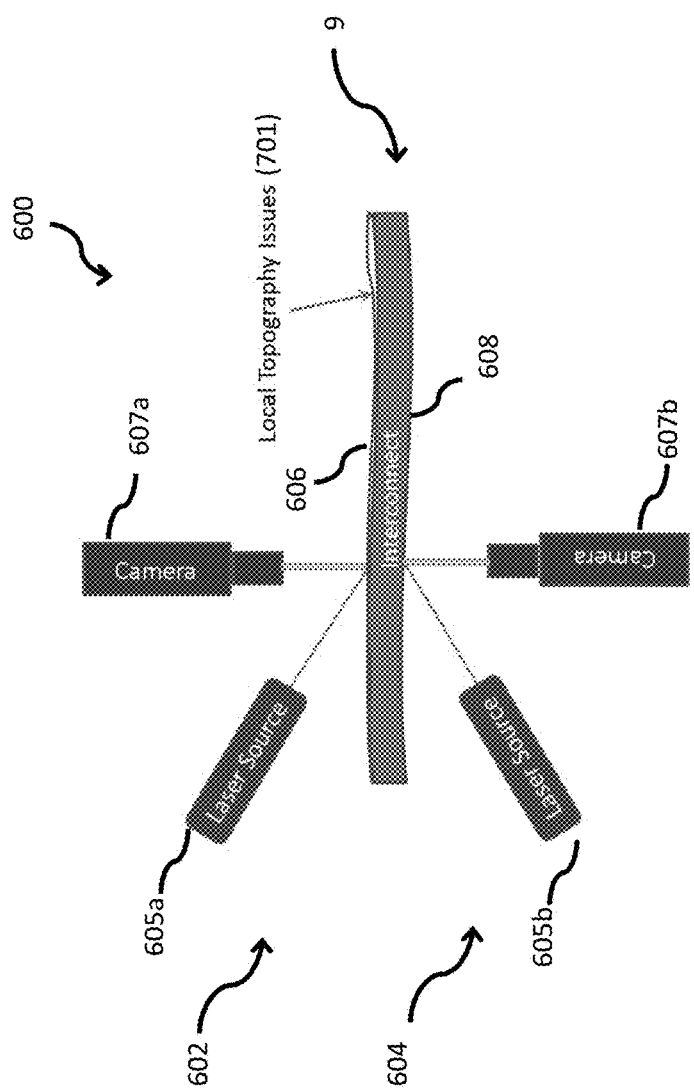
FIG. 7A schematically illustrates a system for measuring local topography variations in an interconnect.
Figure 7B:
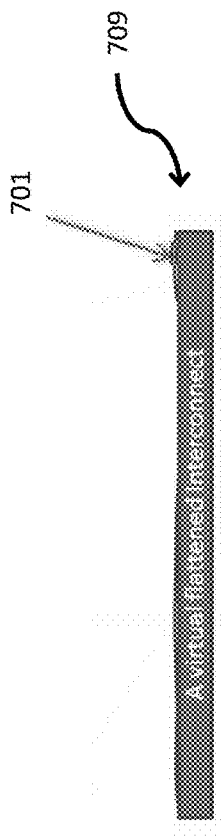
FIG. 7B schematically illustrates an interconnect that has been "virtually flattened" by removing interconnect thickness and curvature to isolate local topography variations.

One problem in measuring the topography of an interconnect arises from the fact that it is difficult to isolate and quantify local variations in the topography in view of the overall variations in the thickness and curvature of the interconnect. This is schematically illustrated in FIG. 7A, which shows an interconnect 9 having local topography issues 701 (i.e., local high and low spots) that are difficult to detect due to the overall curvature of the interconnect 9. In one embodiment, an optical scanning system 600 such as described above in connection with FIG. 6 may be used to scan opposite surfaces 606, 608 of the interconnect 9 and measure the overall thickness and curvature of the interconnect, as described above. Using various algorithms, the calculated thickness and curvature values for the interconnect may then be applied to the raw measurement data to generate a representation of a virtual "flattened" interconnect 709, as schematically illustrated in FIG. 7B. The "flattened" interconnect 709 corrects for variations due to interconnect thickness and curvature, and provides a measurement of local topographical variations, such as topography issue 701. These local topography issues 701 (i.e., local high and low spots) may then be identified and quantified. An interconnect having a local topography variation meeting a predetermined threshold can be flagged as defective.

In this manner, various local topographical variations of an interconnect may be accurately and rapidly measured. A typical measurement may take less than 10 seconds, such as 5 seconds or less (e.g., 1-4 seconds).

Measuring Dimensions of a Fuel Cell Component Using Line Scan and/or Matrix Camera One of the keys to an efficient fuel cell system is using conforming parts in the construction of the fuel cell stacks. The use of powder metallurgy techniques to fabricate the fuel cell interconnects is challenging and can result in significant dimensional variability in the interconnects, such as from batch to batch, vendor to vendor or over time through die wear. Similar dimensional variability may exist in the fuel cell electrolytes, which are typically made of fired ceramic material.

Thus, when constructing a fuel cell stack or multi-stack fuel cell power system, it is desirable to use components, such as interconnects and electrolytes, that share similar dimensional characteristics, such as component length and width, fuel hole size and location, and other dimensions important to the form, fit and function of the components.

Various embodiments include methods of measuring the dimensions of a component of a fuel cell system, such as an interconnect or an electrolyte, using a line scan camera and/or a matrix camera.

Figure 8:
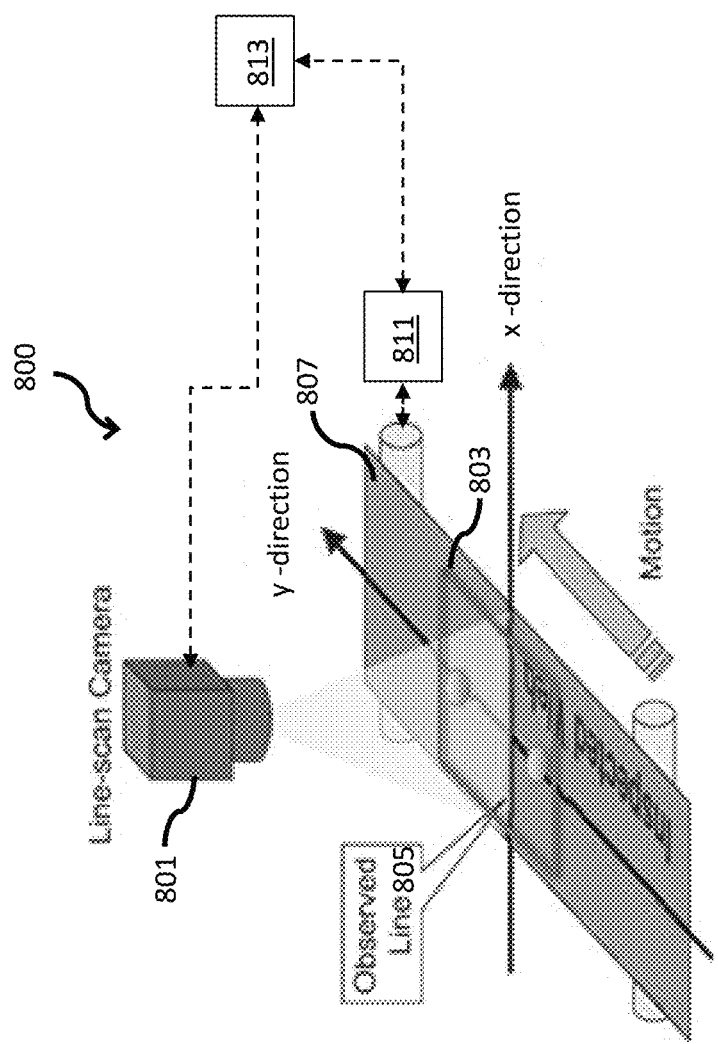
FIG. 8 schematically illustrates a line scan system for measuring dimensions of a fuel cell component.

A system 800 for measuring the dimensions of a fuel cell component 803 using a line scan camera 801 is shown in FIG. 8. A line scan camera 801 captures a single line 805 (i.e., 1 pixel) of image data in a first direction (i.e., the y-direction in FIG. 8), and a plurality of pixels (e.g., up to 12,000 pixels) of image data in a second direction (i.e., the x-direction in FIG. 8). The fuel cell component 803 may be moved through the field of view of the camera 801 to image all or a portion of the component. The component 803 may be moved on a belt 807 or similar support, as shown in FIG. 8. A drive mechanism 811 may control the movement of the belt 807. Alternatively or in addition, the camera 801 may be moved relative to the component 803 to perform the scan. A controller 813 may control the operation of the camera 801 and drive mechanism 811. The controller 813 may be a logic device (i.e., computer) having a memory and a processor coupled to the memory, wherein the processor can be configured with processor-executable instructions for performing various functions, including image processing functions and fuel cell component measurement functions as described below.

Using an encoder, the various lines of image data captured by the camera 801 may be reassembled into a combined image representation of the fuel cell component 803. The resultant combined image may be post-processed (e.g., by controller 813) to measure one or more dimensions of the component, which in the case of fuel cell electrolytes and interconnects can include fuel hole dimensions, hole positions and/or overall length and width dimensions.

Figure 9:
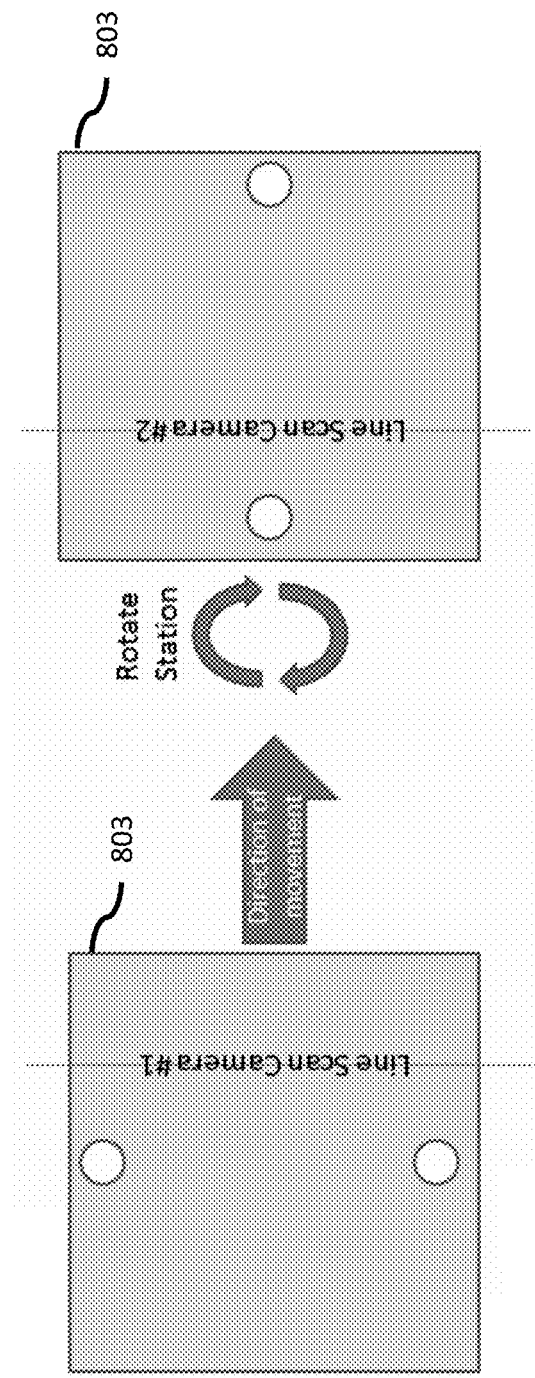
FIG. 9 schematically illustrates a method of improving the accuracy of a line scan measurement by performing two scans of a fuel cell component with a 90° change in orientation.

One drawback to this method is that the combined image is more accurate in the x-axis direction (i.e., the direction of the observed line 805) than in the y-axis direction (i.e., the direction of component 803 travel). In various embodiments, the accuracy may be improved by performing an initial line scan with the component 803 in a first orientation, such as shown in FIG. 9A, and performing a second line scan with the component 803 in a second orientation, such as shown in FIG. 9B, wherein the second orientation is rotated by 90° with respect to the first orientation. The images from the first line scan and the second line scan may be combined, and the resultant combined image may be used to measure one or more dimensions of the component 803, such as fuel hole dimensions, fuel hole locations and/or overall component 803 dimensions.

In one embodiment, the component 803 may be rotated by 90° between the initial scan and the second scan. In another embodiment, the component 803 may move in a first direction with respect to a line scan camera 801 during the initial scan (such as on a belt 807 as shown in FIG. 8), and may move in a second direction with respect to a line scan camera 801 during the second scan (e.g., on a different belt), wherein the second direction is perpendicular to the first direction. The line scan camera 801 used for the second scan may be the same camera or a different camera as used for the initial scan.

Figure 10A:
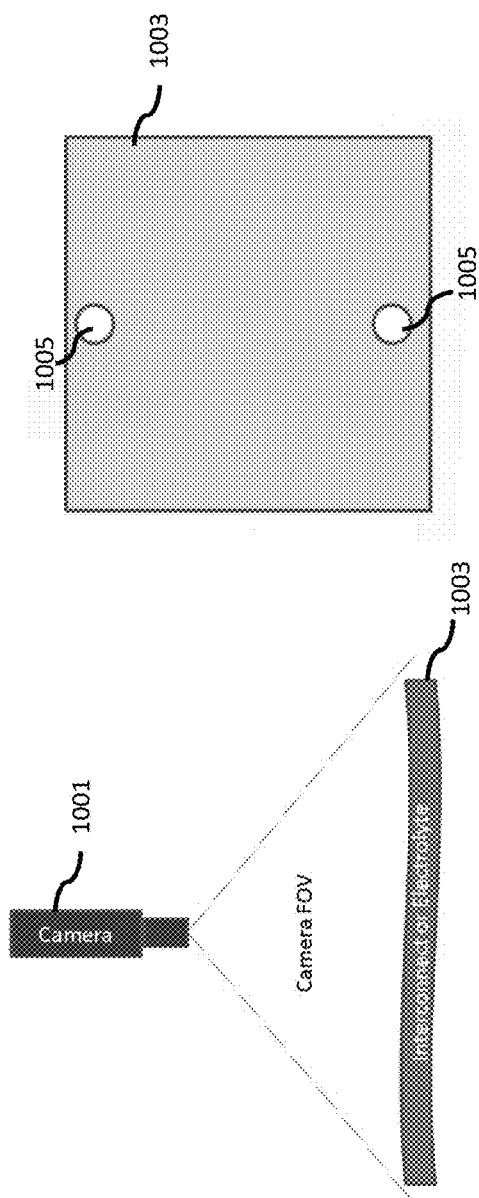
FIG. 10A schematically illustrates a matrix camera for measuring dimensions of a fuel cell component.
Figure 10B:
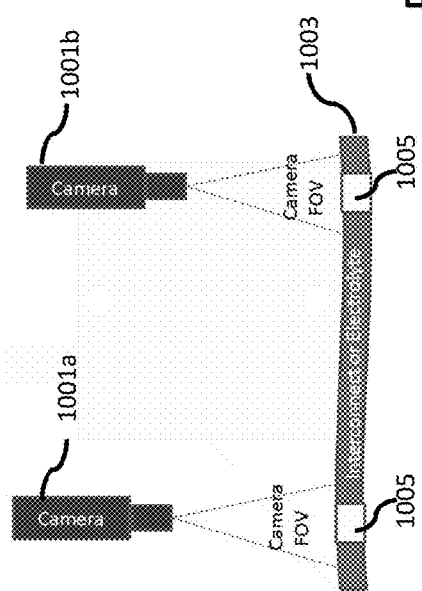
FIG. 10B schematically illustrates a system for measuring the dimensions of a fuel cell component that includes two matrix cameras positioned above the fuel holes of the component.

Further embodiments include methods of measuring the dimensions of a component of a fuel cell system, such as an interconnect or an electrolyte, using a matrix camera. An example of a matrix camera 1001 is illustrated in FIG. 10A. A matrix camera 1001 is a high-resolution camera (e.g., a CCD camera) that captures image data in both the x- and y-dimensions. A matrix camera 1001 can acquire an overall snapshot of a fuel cell component 1003 requiring evaluation, as shown in FIG. 10A. The component 1003 may be an interconnect or an electrolyte, and may include one or more holes 1005 (e.g., fuel holes in the case of a fuel cell stack internally manifolded for fuel). If the camera's resolution is high enough for a part dimension to be measured, a single shot (image) may be sufficient. If the dimensional accuracy required needs to be higher, multiple cameras can be utilized, and/or the portion(s) of the component requiring high-resolution measurement may be moved under a focused camera, such as shown in FIG. 10B. For example, if a high accuracy measurement of the fuel holes 1005 is required, the component 1003 (e.g., an interconnect or electrolyte) can be moved and paused under a focused camera 1001*a*, 1001*b* for imaging each of the holes.

The image(s) of a fuel cell component acquired by one or more matrix cameras may be post-processed to measure various dimensions of the component, such as fuel hole dimensions, hole positions and overall part dimensions.

In either of the line scan or matrix camera embodiments, the measured dimensions of the component may be compared with a reference dimension or dimension range. Where a measured dimension deviates from a reference dimension or dimension range by a predetermined amount, the component may be flagged as defective.

In this manner, various dimensions of a fuel cell component may be accurately and rapidly measured. A typical measurement may take less than 10 seconds, such as 5 seconds or less (e.g., 1-4 seconds).

The various measurement techniques described herein may be used independently or in conjunction with one another. For example, a fuel cell component may undergo a single optical scan, and the resulting three-dimensional topographical representation of the component may be used to determine various properties of the component, such as flow channel volume, the existence of various defects, including crack defects and coating defects, thickness and curvature measurements and/or local topography variations. Alternatively, the same fuel cell component may undergo a series of optical scans to determine various properties of the component. Additionally, the three-dimensional optical scanning methods and systems described herein may be used in conjunction with a line scan and/or matrix camera imaging method for measuring one or more dimensions of a fuel cell component.

The foregoing method descriptions are provided merely as illustrative examples and are not intended to require or imply that the steps of the various embodiments must be performed in the order presented. As will be appreciated by one of skill in the art the order of steps in the foregoing embodiments may be performed in any order. Words such as "thereafter," "then," "next," etc. are not necessarily intended to limit the order of the steps; these words may be used to guide the reader through the description of the methods. Further, any reference to claim elements in the singular, for example, using the articles "a," "an" or "the" is not to be construed as limiting the element to the singular.

The preceding description of the disclosed aspects is provided to enable any person skilled in the art to make or use the present invention. Various modifications to these aspects will be readily apparent to those skilled in the art, and the generic principles defined herein may be applied to other aspects without departing from the scope of the invention. Thus, the present invention is not intended to be limited to the aspects shown herein but is to be accorded the widest scope consistent with the principles and novel features disclosed herein.

What is claimed is:

1. A method for measuring a property of an interconnect for a fuel cell stack, the interconnect comprising a plurality of ribs and a plurality of channels between the ribs on a first surface of the interconnect, the method comprising:
    performing a first three-dimensional optical scan of at least a portion of the first surface of the interconnect to produce a first three-dimensional representation of the topography of the at least a portion of the first surface, wherein performing the first three-dimensional optical scan comprises detecting optical radiation reflected from the first surface of the interconnect;
    performing a second three-dimensional optical scan of at least a portion of a second surface of the interconnect opposite the first surface to produce a second three-dimensional representation of the topography of the at least a portion of the second surface, wherein performing the second three-dimensional optical scan comprises detecting optical radiation reflected from the second surface of the interconnect;
    measuring at least one of the thickness and curvature of the interconnect based on the first and second three-dimensional representations;
    generating a virtual flattened representation of the interconnect based on at least one of a measured thickness and a measured curvature of the interconnect, the virtual flattened representation being configured to correct for variations due to at least one of the thickness and the curvature of the interconnect; and
    measuring topography of the interconnect based on the virtual flattened representation.

2. The method of claim 1, further comprising determining flow volume values of the plurality of channels by measuring a series of cross sectional areas of each channel of the plurality of channels on the first surface of the interconnect.

3. The method of claim 1, wherein the optical scan comprises an optical triangulation scan.

4. The method of claim 3, wherein the optical triangulation scan comprises a laser triangulation scan.

5. The method of claim 1, further comprising detecting a defect in the interconnect based on the virtual flattened representation, wherein the defect comprises one or more of a lateral crack, a missing rib, a hole and a void area.

6. The method of claim 5, wherein the interconnect comprises a coating over the surface of the component, and the defect comprises a coating defect.

7. The method of claim 6, wherein the coating comprises at least one of a lanthanum strontium manganite (LSM) perovskite and a manganese cobalt oxide (MCO) spinel coating.

8. The method of claim 1, wherein the virtual flattened representation is configured to correct for variation in both the thickness and the curvature of the interconnect.

9. A method for measuring a property of a component of a fuel cell system, comprising:
    performing a first three-dimensional optical scan of at least a portion of a first surface of the component to produce a first three-dimensional representation of the topography of the at least a portion of the first surface, wherein performing the first three-dimensional optical scan comprises detecting optical radiation reflected from a plurality of positions on the first surface of the component;
    performing a second three-dimensional optical scan of at least a portion of a second surface of the component opposite the first surface to produce a second three-dimensional representation of the topography of the at least a portion of the second surface, wherein performing the second three-dimensional optical scan comprises detecting optical radiation reflected from a plurality of positions on the second surface of the component;
    measuring at least one of the thickness and curvature of the component based on the first and second three-dimensional representations;
    generating a virtual flattened representation of the component based on at least one of a measured thickness and a measured curvature of the component, the virtual flattened representation being configured to correct for variations due to at least one of the thickness and the curvature of the component; and
    measuring topography of the component based on the virtual flattened representation.

10. The method of claim 9, wherein the virtual flattened representation is configured to correct for variations in both the thickness and the curvature of the component.

11. The method of claim 9, wherein measuring the topography comprises identifying localized high and low spots.

12. The method of claim 9, wherein the component comprises an interconnect for a fuel cell stack.

13. The method of claim 9, wherein the component comprises a fuel cell electrolyte.

14. The method of claim 9, wherein the first and second three-dimensional optical scans are preformed simultaneously.

\* \* \* \* \*